United States Patent [19]

Dirlikov

[11] Patent Number: 4,474,970
[45] Date of Patent: Oct. 2, 1984

[54] METHOD OF MAKING 3,4,5-TRITHIATRICYCLO[5.2.1.0$^{2,6}$]DECANES AND DERIVATIVES THEREOF

[75] Inventor: Stoil K. Dirlikov, Midland, Mich.

[73] Assignee: The Dow Chemical Company, Midland, Mich.

[21] Appl. No.: 373,387

[22] Filed: Apr. 30, 1982

[51] Int. Cl.$^3$ ............................................. C07C 341/00
[52] U.S. Cl. ....................................................... 549/31
[58] Field of Search ........................................... 549/31

[56] References Cited

U.S. PATENT DOCUMENTS 4,097,474 6/1978 Askew et al. ...................... 549/31 X Primary Examiner—Richard Raymond
Attorney, Agent, or Firm—Paul D. Hayhurst

[57] ABSTRACT 3,4,5-Trithiatricyclo[5.2.1.0$^{2,6}$]decanes and derivatives are prepared in high yield by contacting a bicyclo[2.2.1]hept-2-ene compound and sulfur in the presence of a solvent, and a catalytic amount of sulfide ions.

21 Claims, No Drawings

METHOD OF MAKING 3,4,5-TRITHIATRICYCLO[5.2.1.0$^{2,6}$]DECANES AND DERIVATIVES THEREOF

BACKGROUND OF THE INVENTION

This invention relates to a method for the production of 3,4,5-trithiatricyclo[5.2.1.0$^{2,6}$]decanes and the 3,4,5-trithiapolycyclo derivatives thereof.

The interaction of sulfur with organic compounds has been known for many years to generally result in complex polysulfide compounds. More specifically, and recently, it was shown in U.S. Pat. No. 3,586,700 that ammonia and certain other organic amines could catalyze the interaction of sulfur with certain bicyclo[2.2.1-]hept-2-ene compounds to produce a novel class of 3,4,5-trithiatricyclo[5.2.1.0$^{2,6}$]decane compounds. It was also shown that this catalytic reaction occurs only in the presence of certain highly polar organic solvents and that the sulfuration occurs only across the double bond in the bicyclo[2.2.1]hept-2-ene ring structure.

U.S. Pat. No. 4,033,982 also discloses a method for the preparation of the subject compounds. That method requires the use of a phenol and a base and can be carried out in the absence or presence of an inert organic solvent. It is disclosed that the base is employed in order to form, in the presence of the phenol, a metal phenoxide. Sodium sulfide is listed as a representative base.

U.S. Pat. No. 3,882,031 discloses a method of sulfurizing bicyclo[2.2.1]hept-2-enes for use as lubricant additives. The sulfurization is carried out in the absence of a solvent or in the presence of a non-polar solvent. Sulfide ions are described as a less-than-preferred catalyst, and the method typically employs a solubilizing agent to assist in increasing the proportion of oil-soluble constituents in the product. Further, pyridine is listed as an amine catalyst.

It would be highly desirable to possess a high yield process for the preparation of 3,4,5-trithiatricyclodecanes and derivatives thereof which, in addition to providing higher yields than the methods of the prior art, did not require an amine catalyst, a phenol, or a solubilizing agent.

SUMMARY OF THE INVENTION

The present invention is such a method of preparing 3,4,5-trithiapolycyclo compounds in high yields. According to the method of the present invention, 3,4,5-trithiapolycyclo compounds, as hereinafter described, are produced by contacting sulfur and a bicyclo[2.2.1-]hept-2-ene, or a derivative thereof, in the presence of a solvent and a catalytic amount of sulfide ions under the proper reaction conditions. Surprisingly, the method of the present invention produces the title compounds in pure form and in higher yields than the methods of the prior art. An additional advantage of the method of the present invention over the prior art methods is that the instant method obviates the need to use large amounts of phenol, said amounts being, for example, equimolar to the bicyclo[2.2.1]hept-2-ene starting materials. A further advantage of the present invention is that substantially quantitative yields are often obtainable, thus providing the subject product compounds in pure or substantially pure form. Another advantage of the method of the present invention is the lack of formation of oligomers and polymers, which polymers detract from the purity of the product and cause extensive purification steps to be taken to obtain the desired pure product compounds. The products of the method of the present invention are useful in several applications, including uses as cross-linking agents, plasticizers, thermal stabilizers, antioxidants, paving and roofing binders, and monomers.

DETAILED DESCRIPTION OF THE INVENTION

The bicyclo[2.2.1]hept-2-ene compounds that are suitable for use in this invention are generally described by the formula

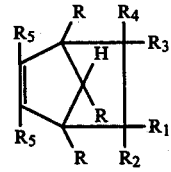

wherein each R, $R_1$, $R_2$, $R_3$ and $R_4$ is independently hydrogen, halogen, alkyl of from 1 to about 15 carbon atoms, aryl of from about 6 to about 15 carbon atoms, or cycloalkyl of from about 4 to about 10 carbon atoms; $R_1$ and $R_3$ may further be independently chosen from alkenyl of from 2 to about 10 carbon atoms, hydroxyl, hydroxyalkyl having from 1 to about 10 carbon atoms, dialkylamino having from 1 to about 10 carbon atoms, dialkylaminoalkyl wherein the alkyl groups have from 1 to about 4 carbon atoms, and alkoxy having from 1 to about 10 carbon atoms; each $R_5$ is independently hydrogen or alkyl of from 1 to about 15 carbon atoms; $R_1$ and $R_2$ when taken together and $R_3$ and $R_4$ when taken together are alkylidene of from 1 to about 6 carbon atoms; $R_1$ and $R_3$ when taken together are —CHYCH=CY— wherein Y is hydrogen or methyl. These compounds are also described in U.S. Pat. Nos. 3,586,700 and 4,033,982, the teachings of which, with respect to these compounds, are incorporated herein by reference. Preferred bicyclo[2.2.1]hept-2-ene compounds include, for example, dicyclopentadiene, bicyclo[2.2.1]hept-2-ene and 5-ethenyl-bicyclo[2.2.1]hept-2-ene. Dicyclopentadiene is the most preferred bicyclo[2.2.1]hept-2-ene compound.

The source of sulfur can be elemental sulfur, which is preferred, or polysulfide ions as described in U.S. Pat. No. 4,033,982, the teaching of which, with respect to all sources of sulfur, is incorporated herein by reference.

Theoretically, 3 moles of sulfur atoms are necessary per mole of bicyclo[2.2.1]hept-2-ene compound in order to produce the corresponding trithiane. Preferably, from about 2.8 to about 3 g-atoms of sulfur are employed per g-mole of bicyclo[2.2.1]hept-2-ene compound. Larger or smaller amounts of sulfur can be used, if desired, however, pentathiane formation may be observed at sulfur/bicyclo[2.2.1]hept-2-ene compound ratios greater than 3.

Sulfide ions catalyze the reaction of the present invention. Examples of suitable catalysts include alkali metal sulfides, alkaline earth metal sulfides, alkaline earth metal mercaptides and alkali metal mercaptides. Preferred catalysts include anhydrous sodium sulfide, sodium sulfide nonahydrate ($Na_2S.9H_2O$) and sodium phenylthiolate. In the practice of the present invention, it is preferred that the catalyst be in solution. Any amount of sulfide ions may be used as long as the reaction is catalyzed by those ions. Typically, from about $1 \times 10^{-10}$ to about 1 mole of sulfide ions are employed per mole of bicyclo[2.2.1]hept-2-ene compound employed; preferably from about $1 \times 10^{-5}$ to about 0.01 mole of sulfide ions are employed per mole of bicyclo[2.2.1]hept-2-ene compound. Most preferably, the amount of sulfide ions will range from about 0.001 to about 0.01 mole of sulfide ions per mole of bicyclo[2.2.1]hept-2-ene compound.

Sulfide ions are advantageously employed in the form of a soluble sulfide compound. For the purposes of the present invention, the term soluble sulfide compound refers to sulfide ion-containing compounds which are soluble in one of the possible solvent systems which are suitable for use in the method of the present invention. Thus, almost any sulfide ion-containing compound is a soluble sulfide compound because there are many solvent systems which are capable of solvating the various components of the reaction mixture, i.e., catalyst and reactants, to form a homogeneous mixture. For example, sodium sulfide is soluble in many polar solvents, but is insoluble in most non-polar solvents at the typically employed reaction temperatures.

A wide number of solvents and combinations of solvents may be employed in the practice of the present invention. Polar organic solvents and combinations of polar and other inert organic co-solvents are preferred. Typical polar organic solvents and combinations of solvents are described in U.S. Pat. No. 3,586,700, the teachings of which, with respect to solvents, are incorporated herein by reference. An example of a preferred combination of solvents is dimethylformamide in combination with pyridine. Non-polar or inert organic solvents may be used alone provided that, if the catalyst employed is not soluble in said solvent, a phase-transfer agent is employed therewith for the purpose of aiding the dissolution of the catalyst. Any phase-transfer agent which aids the dissolution of the catalyst into the reaction solution may be employed. Several suitable phase-transfer agents are well-known, including for example, dibenzo-18-crown-6 ether and bis(triphenylphosphine)iminium chloride. Typical non-polar solvents include aliphatic and aromatic hydrocarbons such as heptane, cyclohexane, 3-methylpentane, isooctane, cumene, toluene and the like. Toluene is an example of a preferred non-polar solvent.

Any amount of solvent may be employed as long as it is sufficient to dissolve the final product. Typically, from about 500 to about 2000 ml of solvent are employed per mole of bicyclo[2.2.1]hept-2-ene compound. Preferably, from about 800 to about 1200 ml of solvent are employed per mole of bicyclo[2.2.1]hept-2-ene compound.

In general, any reaction temperature can be employed wherein the thermal reaction kinetics are not deleterious to reaction rates, reaction time, yield and/or conversion of the bicyclo[2.2.1]hept-2-ene compounds to the desired 3,4,5-trithiapolycyclo compounds. Typically, the reaction temperatures can be varied widely, however, they often fall within the range of from about 20° C. to about 150° C. and preferably the reaction is conducted within the temperature range of from about 90° C. to about 120° C. The reaction is typically performed at atmospheric pressure, although sub- or super-atmospheric pressures may be employed if desired.

Any reaction period can be employed, however, generally effective reaction periods fall within the range of from about 1 hour to about 20 hours. The process is preferentially carried out in the presence of an inert atmosphere of nitrogen in order to exclude from the reaction medium any oxygen or oxidizing agents which are well-known to oxidize organic sulfides to sulfoxides or sulfones among other undesirable reaction products.

When the reactants, catalyst and solvent(s) are properly combined under reaction conditions as hereinbefore specified, a 3,4,5-trithiapolycyclo product will be formed in high yield. The 3,4,5-trithiapolycyclo product compounds of the present invention are generally described by the formula:

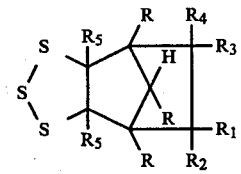

wherein the substituents are as previously described. These products are well-known and are generally described in U.S. Pat. Nos. 3,586,700, and 4,033,982 the teachings of which, with respect to the structures of 3,4,5-trithiapolycyclo product compounds, are incorporated herein by reference.

The crude product of the reaction may be treated by known methods, such as those described in Example 1, to recover the desired products. For the purpose of this invention, the term crude product of the reaction means the mass of material in the reactor at the end of the chosen reaction time and before any purification steps have been taken. Further, for the purposes of the present invention, the term high yield means a yield of a 3,4,5-trithiapolycyclo compound which is higher than those yields reported previously in the art. Preferably this yield will be greater than about 93 percent. Most preferably the yield will be greater than about 95 percent.

The following examples and comparative experiments are given to illustrate the invention and should not be construed as limiting its scope.

EXAMPLE 1

Three g-atoms of sulfur (96.19 g), 1.05 moles of dicyclopentadiene (138.82 g), 0.0025 mole of sodium sulfide nonahydrate (0.59 g), 950 ml of pyridine and 50 ml of dimethylformamide are added to a 2-liter, three-necked, glass flask which is equipped with means for admitting gas thereto, a stirring means, and a condensing means. Nitrogen gas is admitted to the flask to purge the flask of atmospheric air. The contents of the flask are heated up to 110° C. and that temperature is maintained for 8 hours.

The solvent is then evaporated at 45° C. under a vacuum in a rotary vacuum evaporator to obtain a crystalline crude product. The crude crystals are extracted with pentane in a soxhlet extraction apparatus to separate the pure product from the impurities. The pentane is evaporated to give 222.00 g of yellow crystals of exo-3,4,5-trithiatetracyclo[5.5.1.0$^{2,6}$.0$^{8,12}$]tridec-9-ene. The sulfur content of the yellow crystals is 42.05 weight percent.

The yield is 97.2 mole percent, indicating minimal, or a lack of, formation of polysulfides from the starting materials. The melting point of the crystals is 69.5° C.–70.0° C. Further purification of the crystals could be achieved by vacuum distillation or further extraction/crystallization steps.

EXAMPLE 2

The ingredients of Example 1, except for the sodium sulfide nonahydrate, are added to the flask of Example 1. Nitrogen gas is admitted to the flask and the contents are heated, whereupon a pale yellow solution is formed. The contents of the flask are maintained at 110° C. for one hour. No reaction is observed. The sodium sulfide nonahydrate is added to the pale yellow solution, which almost immediately turns a dark blue-black color, and the reaction is observed to proceed.

Example 2 demonstrates that pyridine, which is used as a solvent for the purposes of the present invention, has no catalytic effect under the reaction conditions indicated herein.

What is claimed is:

1. A method of producing 3,4,5-trithiapolycyclo compounds of the formula:

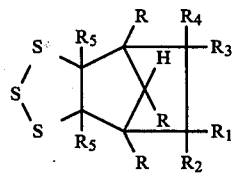

wherein each R, $R_1$, $R_2$, $R_3$ and $R_4$ is independently hydrogen, halogen, alkyl of from 1 to about 15 carbon atoms, aryl of from about 6 to about 15 carbon atoms, or cycloalkyl of from about 4 to about 10 carbon atoms; $R_1$ and $R_3$ may further be independently chosen from alkenyl of from 2 to about 10 carbon atoms, hydroxyl, hydroxyalkyl having from 1 to about 10 carbon atoms, dialkylamino having from 1 to about 10 carbon atoms, dialkylaminoalkyl wherein the alkyl groups have from 1 to about 4 carbon atoms, and alkoxy having from 1 to about 10 carbon atoms; each $R_5$ is independently hydrogen or alkyl of from 1 to about 15 carbon atoms; $R_1$ and $R_2$ when taken together and $R_3$ and $R_4$ when taken together are alkylidene of from 1 to about 6 carbon atoms; $R_1$ and $R_3$ when taken together are —CHYCH=CY— wherein Y is hydrogen or methyl; comprising contacting sulfur and a compound of the formula:

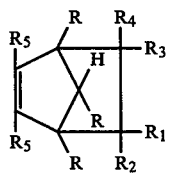

wherein the substituents are as previously described, in the presence of a catalytic amount of a soluble sulfide compound and under such conditions that a 3,4,5-trithiapolycyclo compound, as hereinbefore described, is formed in a yield which is greater than about 93 percent before any steps are taken to purify the crude product of the reaction.

2. The method of claim 1 wherein the soluble sulfide compound comprises an alkali metal or alkaline earth metal cation and a sulfide or mercaptide anion.

3. The method of claim 2 wherein the 3,4,5-trithiapolycyclo compound is exo-3,4,5-trithiatetracyclo[5.5.1.0$^{2,6}$.0$^{8,12}$]tridec-9-ene, 8-ethenyl-exo-3,4,5-trithiatricyclo[5.2.1.0$^{2,6}$]decane, or exo-3,4,5-trithiatricyclo[5.2.1.0$^{2,6}$]decane.

4. The method of claim 1 wherein the solvent comprises a non-polar solvent and further wherein a phase-transfer agent is optionally employed.

5. The method of claim 1 wherein the solvent comprises a polar solvent.

6. The method of claim 5 wherein the soluble sulfide compound is anhydrous sodium sulfide or sodium sulfide nonahydrate.

7. The method of claim 6 wherein the 3,4,5-trithiatricyclo compound is exo-3,4,5-trithiatetracyclo[5.5.1.0$^{2,6}$.0$^{8,12}$]tridec-9-ene.

8. The method of claim 7 wherein the polar solvent comprises a mixture of pyridine and dimethylformamide.

9. The method of claim 5 wherein the contacting is in the substantial absence of phenols and the temperature is from about 20° C. to about 150° C.

10. The method of claim 1 wherein the contacting is conducted within the temperature range of from about 20° C. to about 150° C.

11. A method of producing 3,4,5-trithiapolycyclo compounds of the formula:

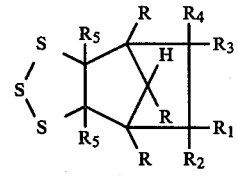

wherein each R, $R_1$, $R_2$, $R_3$ and $R_4$ is independently hydrogen, halogen, alkyl of from 1 to about 15 carbon atoms, aryl of from about 6 to about 15 carbon atoms, or cycloalkyl of from about 4 to about 10 carbon atoms; $R_1$ and $R_3$ may further be independently chosen from alkenyl of from 2 to about 10 carbon atoms, hydroxyl, hydroxyalkyl having from 1 to about 10 carbon atoms, dialkylamino having from 1 to about 10 carbon atoms, dialkylaminoalkyl wherein the alkyl groups have from 1 to about 4 carbon atoms, and alkoxy having from 1 to about 10 carbon atoms; each $R_5$ is independently hydrogen or alkyl of from 1 to about 15 carbon atoms; $R_1$ and $R_2$ when taken together and $R_3$ and $R_4$ when taken together are alkylidene of from 1 to about 6 carbon atoms; $R_1$ and $R_3$ when taken together are —CHYCH=CY— wherein Y is hydrogen or methyl; comprising contacting sulfur and a compound of the formula:

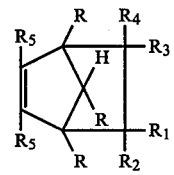

wherein the substituents are as previously described, in the presence of a catalytic amount of a soluble sulfide compound and in the substantial absence of phenols and in the presence of a polar solvent and under such conditions that a 3,4,5-trithiapolycyclo compound, as hereinbefore described, is formed.

12. The method of claim 11 wherein the solvent comprises a polar aprotic solvent.

13. The method of claim 12 wherein the solvent comprises dimethylformamide.

14. The method of claim 11 wherein a 3,4,5-trithiapolycyclo compound is produced in a yield which is greater than about 93 percent before any steps are taken to purify the crude product of the reaction.

15. The method of claim 14 wherein the solvent comprises a mixture of pyridine and dimethylformamide.

16. A method of producing 3,4,5-trithiapolycyclo compounds of the formula:

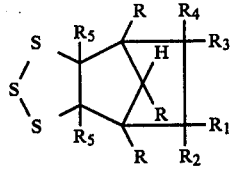

wherein each R, $R_1$, $R_2$, $R_3$ and $R_4$ is independently hydrogen, halogen, alkyl of from 1 to about 15 carbon atoms, aryl of from about 6 to about 15 carbon atoms, or cycloalkyl of from about 4 to about 10 carbon atoms; $R_1$ and $R_3$ may further be independently chosen from alkenyl of from 2 to about 10 carbon atoms, hydroxyl, hydroxyalkyl having from 1 to about 10 carbon atoms, dialkylamino having from 1 to about 10 carbon atoms, dialkylaminoalkyl wherein the alkyl groups have from 1 to about 4 carbon atoms, and alkoxy having from 1 to about 10 carbon atoms; each $R_5$ is independently hydrogen or alkyl of from 1 to about 15 carbon atoms; $R_1$ and $R_2$ when taken together and $R_3$ and $R_4$ when taken together are alkylidene of from 1 to about 6 carbon atoms; $R_1$ and $R_3$ when taken together are —CHYCH=CY— wherein Y is hydrogen or methyl; comprising contacting sulfur and a compound of the formula:

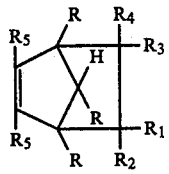

wherein the substituents are as previously described in the presence of a catalytic amount of a soluble sulfide compound and in the presence of a polar aprotic solvent under such conditions that a 3,4,5-trithiapolycyclo compound, as hereinbefore described, is formed.

17. The method of claim 16 wherein the trithiapolycyclo compound is produced in a yield which is greater than about 93 percent, measured before any steps are taken to purify the crude product of the reaction.

18. The method of claim 17 wherein the yield is greater than about 95 percent, measured before any steps are taken to purify the crude product of the reaction.

19. The method of claim 18 wherein the 3,4,5-trithiapolycyclo compound is exo-3,4,5-trithiatricyclo[5.2.1.0$^{2,6}$]decane.

20. The method of claim 16 wherein the contacting is in the substantial absence of phenols.

21. The method of claim 4 wherein the solvent is toluene.

* * * * *